(12) United States Patent
Boon et al.

(10) Patent No.: US 10,743,499 B2
(45) Date of Patent: Aug. 18, 2020

(54) ***BRASSICA OLERACEA* PLANTS WITH DOWNY MILDEW RESISTANT CURDS OR HEADS**

(71) Applicant: Seminis Vegetable Seeds, Inc., St. Louis, MO (US)

(72) Inventors: Meinardus Boon, Scharwoude (NL); Franciscus van den Bosch, Kesteren (NL); Benjamin C. Hunter, St. Louis, MO (US); Gerard N. Koorevaar, Ede (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 16/212,414

(22) Filed: Dec. 6, 2018

(65) Prior Publication Data

US 2019/0191656 A1 Jun. 27, 2019

Related U.S. Application Data

(60) Provisional application No. 62/596,601, filed on Dec. 8, 2017.

(51) Int. Cl.
*C12Q 1/68* (2018.01)
*A01H 6/20* (2018.01)
*A01H 1/04* (2006.01)
*C12Q 1/6895* (2018.01)
*A01H 5/10* (2018.01)

(52) U.S. Cl.
CPC .............. *A01H 6/203* (2018.05); *A01H 1/04* (2013.01); *A01H 5/10* (2013.01); *C12Q 1/6895* (2013.01)

(58) Field of Classification Search
None
See application file for complete search history.

(56) References Cited

PUBLICATIONS

Lee et al. BMC Plant Biology (2015) 15:32.*
Gao et al. Theor Appl Genet (2007)115:277-287.*
Agronomic Spotlight, "Managing Downy Mildew in Broccoli," available at http://www.seminis-us.com/resources/agronomic-spotlights/managing-downy-mildew-in-broccoli/, accessed on Apr. 4, 2019.
Branca, et al., "Sources of Resistance to Downy Mildew (*Peronospora parasitica* (Pers. ex Fr.) Fr.) in Sicilian Germplasm of Cauliflower and Broccoli," Biodiversity and Conservation 14(4): 841-848 (2005).
Coelho and Monteiro, "Expression of Resistance to Downy Mildew at Cotyledon and Adult Plant Stages in *Brassica oleracea* L.," Euphytica 133(3):279-284 (2003).
Coelho, et al., "Pathotypic Diversity of Hyaloperonospora brassicae Collected from *Brassica oleracea*," European Journal of Plant Pathology, 134(4):763-771 (2012).
Farinho, et al., "Mapping of a Locus for Adult Plant Resistance to Downy Mildew in Broccoli (*Brassica oleracea* convar. *italica*)," Theoretical and Applied Genetics 109(7):1392-1398 (2004).
Hoser-Krauze, et al., "Resistance of Cauliflower and Broccoli, (*B. oleracea* L. *otrytis* L.) Seedlings to Downy Mildew, *Peronospora parasitica*," Cruciferae Newsletter 9:92-93 (1984).
Hoser-Krauze, et al., "The Inheritance of Resistance of Some *Brassica oleracea* L. Cultivars and Lines to Downy Mildew—*Peronospora parasitica* (Pers.) ex Fr.," Journal of Applied Genetics 36(1):27-33 (1995).
Jensen, et al., "Seedling and Adult Plant Resistance to Downy Mildew (*Peronospora parasitica*) in Cauliflower (*Brassica oleracea* convar. *botrytis* var. *botrytis*)," Plant Pathology 48(5):604-612 (1999).
Monot and Silue, "Comparison of the Resistance and Susceptibility to Downy Mildew [*Hyaloperonospora parasitica*, constant. (Perspex Fort)] of Nine *Brassica olearacea* Accessions in Laboratory, Seedbed, and Field Screens," Euphytica 169:413-419 (2009).
Singh, et al., "Screening of Cauliflower (*Brassica oleracea* L. var. *botrytis* L.) Germplasm for Resistance to Downy Mildew [*Hyaloperonospora parasitica* Constant (Pers.:Fr) Fr.] and Designing Appropriate Multiple Resistance Breeding Strategies," Journal of Horticultural Science & Biotechnology 88(1):103-109 (2013).
Vicente, et al., "Genetics of Resistance to Downy Mildew in *Brassica oleracea* and Breeding Towards Durable Disease Control for UK Vegetable Production," Plant Pathology 61(3):600-609 (2012).
International Search Report and Written Opinion regarding International Application No. PCT/US2018/064288, dated Apr. 29, 2019.
Genbank Accession No. FI681171.1, dated Mar. 11, 2009.

* cited by examiner

*Primary Examiner* — Medina A Ibrahim
(74) *Attorney, Agent, or Firm* — Dentons US LLP; Alissa Eagle, Esq.

(57) ABSTRACT

The present disclosure provides *Brassica oleracea* plants having curds or heads exhibiting increased resistance to downy mildew. Such plants may comprise novel introgressed genomic regions associated with disease resistance from *Brassica oleracea* MYCOCLP. In certain aspects, compositions, including novel polymorphic markers and methods for producing, breeding, identifying, and selecting plants or germplasm with a disease resistance phenotype are provided.

22 Claims, 1 Drawing Sheet
Specification includes a Sequence Listing.

```
                    SEQUENCE LISTING

<160> NUMBER OF SEQ ID NOS: 16

<210> SEQ ID NO 1
<211> LENGTH: 121
<212> TYPE: DNA
<213> ORGANISM: Brassica oleracea

<400> SEQUENCE: 1
ctcagcatct gaatgctcat caggagcatg cgtttccatg ccaacatcat tcattccttc      60
ytcttcacct cttacccttc tttcattcaa atgagctccc aaggaactct cgtccaaacg     120
a                                                                    121

<210> SEQ ID NO 2
<211> LENGTH: 121
<212> TYPE: DNA
<213> ORGANISM: Brassica oleracea
<220> FEATURE:
<221> NAME/KEY: misc_feature
<222> LOCATION: (84)..(84)
<223> OTHER INFORMATION: n is a, c, g, or t

<400> SEQUENCE: 2
tgggtgattt ataatgaata tgtcttgact actcgcaatt tcattcgcac tgttacagat      60
rtccgcggtg actggttagt tccnatctcc tgcttctgtt gtctgattaa acttcgaagc     120
c                                                                    121

<210> SEQ ID NO 3
<211> LENGTH: 121
<212> TYPE: DNA
<213> ORGANISM: Brassica oleracea
```

-continued

<400> SEQUENCE: 3
gcaatagtgt tgcagctgct tcctctcctt cctctgtagc tgcgatctta gctttcgtgt     60
yctctatcac ctagaaacaa aagatttcat aaccttaaag aacacaaata aaacaacatt    120
t                                                                    121

<210> SEQ ID NO 4
<211> LENGTH: 121
<212> TYPE: DNA
<213> ORGANISM: Brassica oleracea

<400> SEQUENCE: 4
tccaaatcta cctgatctaa agctgcaact acaaaggcat tcactcgctc ttgaacattg     60
waatcaaaca ggtccggatc atccttcatg gattaagaac caaacttatt ataattcata    120
a                                                                    121

<210> SEQ ID NO 5
<211> LENGTH: 121
<212> TYPE: DNA
<213> ORGANISM: Brassica oleracea

<400> SEQUENCE: 5
aactgttgag atgagatact aaaatccata ataacacatt attctaaact tataatgaga     60
racttacgct taaaacattc tttgctacgg atgcacagtt tagcgtcagg gtaaggacta    120
a                                                                    121

<210> SEQ ID NO 6
<211> LENGTH: 121
<212> TYPE: DNA
<213> ORGANISM: Brassica oleracea

<400> SEQUENCE: 6
caggctgttc aaaaaagcaa ttgtccgtag gaagtgcgta gaggaagaaa ctgtgaaata     60
yctccttgac ttcggtaaga ggagaaatat tccggatgtt gtgttgaaga atggtcgcat    120
g                                                                    121

<210> SEQ ID NO 7
<211> LENGTH: 121
<212> TYPE: DNA
<213> ORGANISM: Brassica oleracea
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t

<400> SEQUENCE: 7
aagaactttt gctctttgct ctgtgtatac aaaatgcagt ttagaaaatc aagctatttg     60
rcntgctgtt tacantcgaa agttcgaaac ctacttaccc cctcatactg gcctttaaga    120
c                                                                    121

<210> SEQ ID NO 8
<211> LENGTH: 121
<212> TYPE: DNA
<213> ORGANISM: Brassica oleracea

<400> SEQUENCE: 8
aggtgcggta attgagaaga atggtgttct tgagttaaca caggaagggc actgtttagt       60
yaagcttggt ctggagccga agcttgggaa gttaatatta ggctgcttca gacacagaat      120
g                                                                     121

<210> SEQ ID NO 9
<211> LENGTH: 118
<212> TYPE: DNA
<213> ORGANISM: Brassica oleracea

<400> SEQUENCE: 9
gttaataaga aacaagttag tttgtttgat tatcatatca ggtagagttt tttgtctmtc       60
tacaggtaag tacctcgacc agctggcgtg ctgtagctat ttctcgttgt gcacatgg       118

<210> SEQ ID NO 10
<211> LENGTH: 121
<212> TYPE: DNA
<213> ORGANISM: Brassica oleracea

<400> SEQUENCE: 10
atcgttcata cacaaagcga aagagatagg ggtcgtgtat ctactgggtc acggtgatat       60
magagcaaga aaagattcat ggttcgtcaa gaagctggtc ataaactact tctacgcatt      120
c                                                                     121

<210> SEQ ID NO 11
<211> LENGTH: 121
<212> TYPE: DNA
<213> ORGANISM: Brassica oleracea

<400> SEQUENCE: 11
cgtggcaggc cactttactt agaagtcaga ggaaataaag atgtggaaaa caatattacc       60
ktaactctgg cttctcgggg tcataaagct taaagacaga agaatatctt ctttcgattt      120
t                                                                     121

<210> SEQ ID NO 12
<211> LENGTH: 121
<212> TYPE: DNA
<213> ORGANISM: Brassica oleracea
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t

<400> SEQUENCE: 12
tcagagtaag tatctatcaa tccacttata tcataggaat ttgagaatct gagaaagcga       60
rgcgaattga gaatcgacaa gaaatgatga catccacatg tgtngtttng tgcatcgatg      120
g                                                                     121

<210> SEQ ID NO 13
<211> LENGTH: 84
<212> TYPE: DNA
<213> ORGANISM: Brassica oleracea

<400> SEQUENCE: 13
aattttaaaa acgaaacaaa aattctaatt tacaacgacg gagtgtttga gcattgattt       60

```
ractagcatt tgagttatat gctc                                          84

<210> SEQ ID NO 14
<211> LENGTH: 94
<212> TYPE: DNA
<213> ORGANISM: Brassica oleracea

<400> SEQUENCE: 14
aggttccaag gaccttctag gaacaacaac agccacaggt ttatcatcct ctggattgga   60
raggaggaaa agcttgtact ggtcaccaaa ttta                               94

<210> SEQ ID NO 15
<211> LENGTH: 121
<212> TYPE: DNA
<213> ORGANISM: Brassica oleracea
<220> FEATURE:
<221> NAME/KEY: misc_feature
<222> LOCATION: (103)..(103)
<223> OTHER INFORMATION: n is a, c, g, or t

<400> SEQUENCE: 15
aaagccagcc aaaggccctg cagctgcaac cttcaaaaga tcttctcgtt tgggcacgat   60
rtttttgatt ctcgttatag caccgaaaga acctatctgc cantctaaaa catgttcatc  120
a                                                                  121

<210> SEQ ID NO 16
<211> LENGTH: 121
<212> TYPE: DNA
<213> ORGANISM: Brassica oleracea
<220> FEATURE:
<221> NAME/KEY: misc_feature
<222> LOCATION: (41)..(41)
<223> OTHER INFORMATION: n is a, c, g, or t

<400> SEQUENCE: 16
gtaatttaac cggcacgacg ttctcatgtc gatataaaaa ncgtcacgca tgttctcacg   60
yagtcctttt gaaaatataa cttgaatttt tactacatca aacgtttcct ggtcaaaaac  120
c                                                                  121
```

BRASSICA OLERACEA PLANTS WITH DOWNY MILDEW RESISTANT CURDS OR HEADS

CROSS-REFERENCE TO RELATED APPLICATIONS

This application claims the priority of U.S. Provisional Appl. Ser. No. 62/596,601, filed Dec. 8, 2017, the entire disclosure of which is incorporated herein by reference.

INCORPORATION OF SEQUENCE LISTING

The sequence listing contained in the file named "SEMB031US_ST25.txt", which is 6 kilobytes as measured in Microsoft Windows operating system and was created on Dec. 6, 2018, is filed electronically herewith and incorporated herein by reference.

FIELD OF THE INVENTION

The present invention relates to the field of agriculture and more specifically to methods and compositions for producing *Brassica oleracea* plants with curds or heads exhibiting improved resistance to Downy mildew.

BACKGROUND OF THE INVENTION

Disease resistance is an important trait in agriculture. It is particularly important for varieties used in the production of food crops. In addition to identifying a disease resistance allele, specific markers linked to the resistance allele facilitate the introduction of the allele into cultivated lines. Marker-assisted selection (MAS) in plant breeding methods has made it possible to select plants based on genetic markers linked to traits of interest, in this case, disease resistance. However, identification of markers for tracking and/or introducing desirable traits in plants requires significant effort and as such, the markers are often unavailable even if the gene associated with the trait has been characterized. The difficulty in identifying markers is also complicated by factors such as polygenic or quantitative inheritance, epistasis and an often incomplete understanding of the genetic background underlying expression of a desired phenotype.

SUMMARY OF THE INVENTION

The present disclosure provides a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele. In certain embodiments the plant comprises a first introgressed allele and a second introgressed allele on chromosome 3, wherein the first introgressed allele and the second introgressed allele confers to a curd or head of the plant increased resistance to downy mildew compared to a plant not comprising the alleles. In some embodiments a sample of seed comprising the first introgressed allele and the second introgressed allele was deposited under ATCC Accession Number PTA-124338. In other embodiments the first introgressed allele is flanked in the genome of the plant by marker locus M19 (SEQ ID NO:2) and marker locus M20 (SEQ ID NO:3) on chromosome 3. In yet other embodiments the second introgressed allele is flanked in the genome of the plant by marker locus M31 (SEQ ID NO:4) and marker locus M44 (SEQ ID NO:16) on chromosome 3. In additional embodiments the *Brassica oleracea* plant is a broccoli, cauliflower, sprouting broccoli, Brussels sprouts, white cabbage, red cabbage, savoy cabbage, curly kale cabbage, turnip cabbage or Portuguese cabbage plant. In particular embodiments the plant is homozygous for the first introgressed allele or the second introgressed allele.

The present disclosure also provides a seed that produces a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele. In certain embodiments the seed produces a *Brassica oleracea* plant of a cultivated variety, the plant comprising a first introgressed allele and a second introgressed allele on chromosome 3, wherein the first introgressed allele or the second introgressed allele confers to a curd or head of the plant increased resistance to downy mildew compared to a plant not comprising the first introgressed allele and the second introgressed allele.

The present disclosure additionally provides a plant part of a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele. In certain embodiments the plant part is from a *Brassica oleracea* plant of a cultivated variety, the plant comprising a first introgressed allele and a second introgressed allele on chromosome 3, wherein the first introgressed allele or the second introgressed allele confers to a curd or head of the plant increased resistance to downy mildew compared to a plant not comprising the first introgressed allele and the second introgressed allele. In particular embodiments the plant part is a cell, a seed, a root, a stem, a leaf, a fruit, a flower, a curd, a head or pollen.

The present disclosure further provides an introgression fragment comprising a first chromosomal segment on chromosome 3 from *Brassica oleracea* MYCOCLP flanked by marker M19 (SEQ ID NO:2) and marker M20 (SEQ ID NO:3) and a second chromosomal segment on chromosome 3 from *Brassica oleracea* MYCOCLP flanked by marker M31 (SEQ ID NO:4) and marker M44 (SEQ ID NO:16). In certain embodiments the fragment confers increased resistance to downy mildew. In other embodiments a sample of seed comprising the first chromosomal segment and the second chromosomal segment was deposited under ATCC Accession Number PTA-124338.

The present disclosure also provides a method for producing a cultivated variety of a *Brassica oleracea* plant with a curd or head having improved resistance to downy mildew, comprising introgressing into the plant variety a first chromosomal segment or a second chromosomal segment from *Brassica oleracea* MYCOCLP chromosome 3 that confers improved resistance to downy mildew relative to a plant lacking the introgression. In certain embodiments the introgressing comprises crossing a plant comprising the first or second chromosomal segment with itself or with a second *Brassica oleracea* plant of a different genotype to produce one or more progeny plants, and selecting a progeny plant comprising the chromosomal segment. In other embodiments selecting a progeny plant comprises detecting at least a first allele flanked by marker M19 (SEQ ID NO:2) and marker M20 (SEQ ID NO:3) or a second allele flanked by marker M31 (SEQ ID NO:4) and marker M44 (SEQ ID NO:16). In some embodiments the plant variety is a broccoli, cauliflower, sprouting broccoli, Brussels sprouts, white cabbage, red cabbage, savoy cabbage, curly kale cabbage, turnip cabbage or Portuguese cabbage plant variety. In additional embodiments the progeny plant is an F2, F3, F4, F5 or F6 progeny plant. In particular embodiments the crossing comprises backcrossing. In yet other embodiments the backcrossing comprises from 2-7 generations of backcrosses, for example 2, 3, 4, 5, 6 or 7 generations of backcrosses. In further embodiments the crossing comprises marker-assisted selection. In yet further embodiments a sample of seed comprising the first and second chromosomal segment was deposited under ATCC Accession Number PTA-124338.

The present disclosure further provides a *Brassica oleracea* plant produced by a method for producing a cultivated variety of a *Brassica oleracea* plant with a curd or head having improved resistance to downy mildew, comprising introgressing into the plant variety a first chromosomal segment or a second chromosomal segment from *Brassica oleracea* MYCOCLP chromosome 3 that confers improved resistance to downy mildew relative to a plant lacking the introgression. In addition, the present disclosure provides a method of producing food or feed comprising obtaining a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele, or a *Brassica oleracea* plant produced by a method for producing a cultivated variety of a *Brassica oleracea* plant with a curd or head having improved resistance to downy mildew, comprising introgressing into the plant variety a first chromosomal segment or a second chromosomal segment from *Brassica oleracea* MYCOCLP chromosome 3 that confers improved resistance to downy mildew relative to a plant lacking the introgression, or a part thereof, and producing the food or feed from the plant or part thereof.

The present disclosure also provides a method of selecting a *Brassica oleracea* plant exhibiting resistance downy mildew, comprising crossing a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele, with itself or with a second *Brassica oleracea* plant of a different genotype to produce one or more progeny plants, and selecting a progeny plant comprising the first or second introgressed allele. In certain embodiments selecting the progeny plant comprises identifying a genetic marker genetically linked to the first or second introgressed allele. In other embodiments selecting the progeny plant comprises identifying a genetic marker within or genetically linked to a genomic region between marker locus M19 (SEQ ID NO:2) and marker locus M20 (SEQ ID NO:3) on chromosome 3, or identifying a genetic marker within or genetically linked to a genomic region between marker locus M31 (SEQ ID NO:4) and marker locus M44 (SEQ ID NO:16) on chromosome 3. In additional embodiments selecting a progeny plant further comprises detecting at least one polymorphism at a locus selected from the group consisting of marker locus M33 (SEQ ID NO:5), marker locus M34 (SEQ ID NO:6), marker locus M35 (SEQ ID NO:7), marker locus M36 (SEQ ID NO:8), marker locus M37 (SEQ ID NO:9), marker locus M38 (SEQ ID NO:10), marker locus M39 (SEQ ID NO:11), marker locus M40 (SEQ ID NO:12), marker locus M41 (SEQ ID NO:13), marker locus M42 (SEQ ID NO:14), and marker locus M43 (SEQ ID NO:15). In some embodiments the progeny plant is an F2, F3, F4, F5 or F6 progeny plant. In further embodiments producing the progeny plant comprises backcrossing. In certain embodiments backcrossing comprises from 2-7 generations of backcrossing, for example 2, 3, 4, 5, 6 or 7 generations of backcrossing.

The present disclosure also provides a *Brassica oleracea* plant obtainable by the method of crossing a *Brassica oleracea* plant of a cultivated variety, the plant comprising a first introgressed allele or a second introgressed allele on chromosome 3, wherein the first introgressed allele or the second introgressed allele confers to a curd or head of the plant increased resistance to downy mildew compared to a plant not comprising the first introgressed allele or the second introgressed allele, with itself or with a second *Brassica oleracea* plant of a different genotype to produce one or more progeny plants, and selecting a progeny plant comprising the first or second introgressed allele.

DETAILED DESCRIPTION

Figure 1:
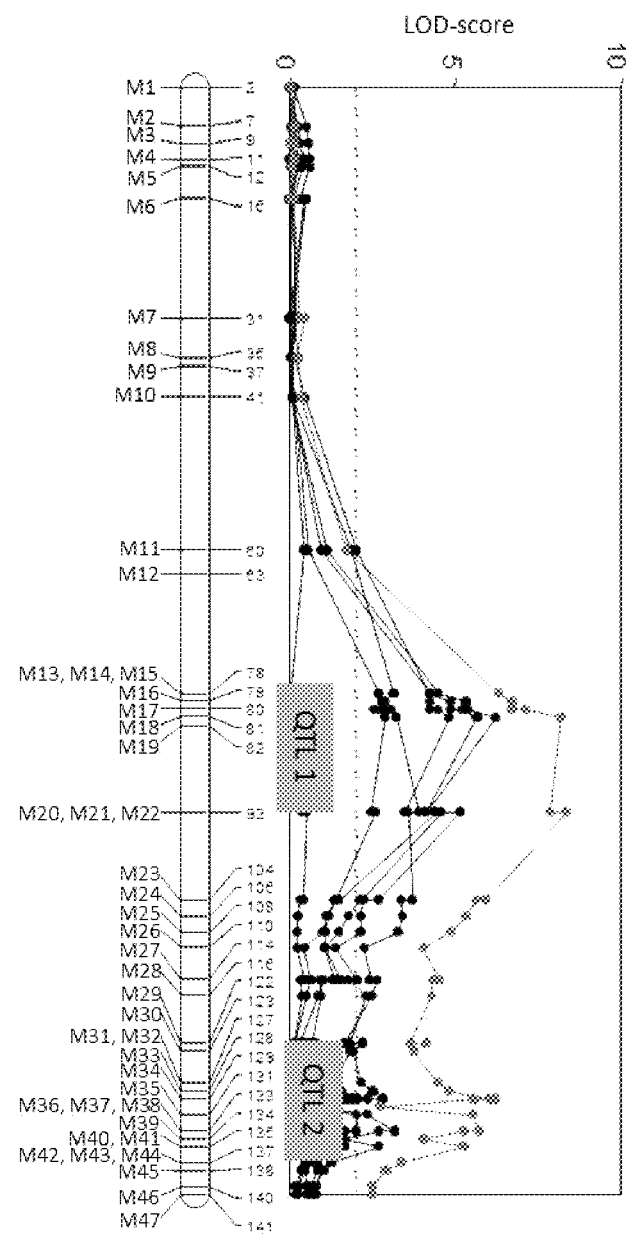
FIG. 1: QTL mapping results for downy mildew resistance in curds. Two QTL are identified on chromosome 3 that together explain 48.1% of the phenotypic variation.

Downy mildew (DM) is caused by an oomycete fungal like pathogen (*Hyaloperonospora brassicae*, also known as *Peronospora parasitica*, also known as *Hyaloperonospora parasitica*). DM is a disease that is found across the globe in many *Brassica* species (*Brassica oleracea*) including, but not limited to, broccoli, cauliflower, cabbage, mustard, radishes, and turnips. DM is more prevalent in regions and seasons with cool, damp weather, high humidity and high levels of dew formation. DM can infect the plants at any stage of growth but is most frequently identified at the seedling stage and on mature plants. Infection can occur at the cotyledon stage, seedling production, mature or adult plant stage and in the curds of cauliflower (*Brassica oleracea* var. *Botrytis*) and broccoli (*Brassica oleracea* var. *Italica*). Although fungicides may be used to control downy mildew infections, it would be preferable to have varieties with resistance to limit the damage from DM at each plant stage. In particular, curd resistance is desirable since the application of fungicides close to harvest stage is limited due to regulations.

Although certain sources of downy mildew resistance in cauliflower have been described in the literature, these sources were generally tested only for cotyledon resistance and not for adult plant or curd resistance. There is no correlation between resistance at the different stages of plant development, and resistance at one stage cannot predict resistance at the other stages. In particular, resistance at the cotyledon stage and/or resistance at the adult plant stage cannot predict resistance in the curd. As a result, one cannot select a source for curd resistance based on foliar tests at either the cotyledon or adult plant stage. Although several sources have been identified that suggest resistance at the cotyledon and adult plant stage, it is unknown whether these same sources would result in resistant curds. Moreover, although certain downy mildew resistance genes have been identified, the genetic position and molecular markers for these genes have not been identified or described.

The experiments to assay for resistance in cauliflower curds require long time periods and incur significant costs. The assay requires that the plants fully develop in the field and that the plants are maintained past the normal harvest time for cauliflower. The trial can require most of a year to conduct. In addition, the downy mildew pressure often varies between and within seasons. Therefore, in order to obtain meaningful and reliable results, several experimental trials must be planted over several different time periods. These types of experimental trials are very labor intensive and require access to large fields.

Once a source is identified, marker assisted breeding would improve and increase the successful introgression of the trait and breeding of cauliflower with downy mildew resistant curds. A trait linked marker is primarily useful when the genetics of a trait is relatively simple and the trait is controlled by a small number of loci, preferably one or two.

The present invention represents a significant advance in that it provides two resistance QTLs that provide increased resistance to downy mildew in curds. In addition, trait linked markers are provided which can be used to introgress the trait and in the breeding of cauliflower with downy mildew resistant curds. The QTLs can be introgressed into elite lines of cultivated crops of *Brassica oleracea*. These crops can include, but are not limited to, cultivated varieties of broccoli, cauliflower, sprouting broccoli, Brussels sprouts, white cabbage, red cabbage, savoy cabbage, curly kale cabbage, turnip cabbage and Portuguese cabbage.

I. *Brassica oleracea* Plants

*Brassica* is a plant genus of the family of brassicaceae (formerly referred to as cruciferae). The members of this genus are also known as cabbage or mustard. The genus *Brassica* comprises a number of commercially and agriculturally important species. Of all those species *Brassica oleracea* is the most diverse containing at least ten different commercial cultivated varieties, including broccoli, cauliflower, sprouting broccoli, Brussels sprouts, white cabbage, red cabbage, savoy cabbage, curly kale cabbage, turnip cabbage and Portuguese cabbage. Breeding between these types is common and easily done because these types, while highly diverse phenotypically, are the same species, which means that a cross between the different types can be made without having to overcome any genetic species barrier. However, significant linkage drag can still occur for intercultivar crosses, especially when crossing between (genetically) distant cultivars (e.g., a cross between white cabbage and broccoli or cauliflower). Thus while the absence of a species barrier allows crosses to be made between all cultivars, it is likely that linkage drag will be associated with such a cross.

II. Genomic Regions, Alleles, and Polymorphisms Associated with Downy Mildew Resistance in *Brassica oleracea* Plants The two downy mildew resistance QTLs of the present invention were identified on chromosome 3. Each QTL provides resistance to downy mildew by itself and when combined the resistance is additive. The recombinant introgression fragments were identified using marker assisted breeding techniques and the introgression fragments generated had sizes of about 11 centiMorgans (cM) and 15 cM. The mapping of these chromosomal segments found that the first QTL for downy mildew resistance is flanked by markers M19 (a SNP change [G/A] at 15,890,285 bp; SEQ ID NO:2) and M20 (a SNP change [T/C] at 10,184,762 bp; SEQ ID NO:3), and the second QTL is flanked by markers M31 (a SNP change [T/A] at 3,226,172 bp; SEQ ID NO:4) and M44 (a SNP change [C/T] at 1,221,810 bp; SEQ ID NO:16). Interstitial markers, such as M33, a SNP change [G/A] at 3,178,026 bp (SEQ ID NO:5), M34, a SNP change [T/C] at 2,874,663 bp (SEQ ID NO:6), M35, a SNP change [A/G] at 2,354,342 bp (SEQ ID NO:7), M36, a SNP change [C/T] at 2,168,486 bp (SEQ ID NO:8), M37, a SNP change [A/C] at 2,212,440 bp (SEQ ID NO:9), M38, a SNP change [C/A] at 1,973,175 bp (SEQ ID NO:10), M39, a SNP change [T/G] at 1,391,141 bp (SEQ ID NO:11), M40, a SNP change [A/G] at 1,932,167 bp (SEQ ID NO:12), M41, a SNP change [A/G] at 2,091,771 bp (SEQ ID NO:13), M42, a SNP change [A/G] at 1,220,020 bp (SEQ ID NO:14), and M43, a SNP change [A/G] at 1,219,392 bp (SEQ ID NO:15), can be used in addition to the flanking markers to select for the second resistance QTL on chromosome 3. In certain embodiments, one or both of the flanking markers for the second resistance QTL are interstitial markers between M31 and M44, such as M33, M34, M35, M36, M37, M38, M39, M40, M41, M42 or M43. The public genome positions are based on version 2.1 of the *Brassica oleracea* genome (plants.ensembl.org/Brassica_oleracea/Info/index).

One of skill in the art will understand that interval values may vary based on factors such as the reference map that is used, the sequencing coverage and the assembly software settings. However, such parameters and mapping protocols are known in the art and one of skill in the art can use the marker sequences provided herein to physically and genetically anchor the introgressions described herein to any given map using such methodology. The novel introgressions of the present invention confer unique significantly improved agronomic properties over previously disclosed downy mildew resistance introgressions.

Thus in certain embodiments the present disclosure provides *Brassica oleracea* plants comprising an introgressed genomic interval flanked by markers M19 and M20 or markers M31 and M44. In other embodiments, the present disclosure provides *Brassica oleracea* plants comprising an introgressed genomic interval flanked by markers M31 and M43, M31 and M42, M31 and M41, M31 and M40, M31 and M39, M31 and M38, M31 and M37, M31 and M36, M31 and M35, M31 and M34, M31 and M33, M33 and M44, M34 and M44, M35 and M44, M36 and M44, M37 and M44, M38 and M44, M39 and M44, M40 and M44, M41 and M44, M42 and M44, M43 and M44, M31 and M44, M33 and M43, M34 and M42, M35 and M41, M36 and M40, or M37 and M39. In further embodiments, the present disclosure provides methods of producing *Brassica oleracea* plants by selecting with any of the above markers.

III. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from *Brassica oleracea* MYCOCLP (ATCC Accession No. PTA_124338), disclosed herein into cultivated *Brassica oleracea* lines. The invention further provides markers for identifying and tracking the novel introgressions disclosed herein during plant breeding.

Markers within or linked to any of the genomic intervals of the present invention can be used in a variety of breeding efforts that include introgression of genomic regions associated with disease resistance into a desired genetic background. For example, a marker within 20 cM, 15 cM, 10 cM, 5 cM, 2 cM, or 1 cM of a marker associated with disease resistance described herein can be used for marker-assisted introgression of genomic regions associated with a disease tolerant phenotype.

*Brassica oleracea* plants comprising one or more introgressed regions associated with a desired phenotype wherein at least 10%, 25%, 50%, 75%, 90%, or 99% of the remaining genomic sequences carry markers characteristic of the germplasm are also provided. *Brassica oleracea* plants comprising an introgressed region comprising regions closely linked to or adjacent to the genomic regions and markers provided herein and associated with downy mildew disease resistance phenotype are also provided.

IV. Development of Disease Resistant *Brassica oleracea* Varieties

For most breeding objectives, commercial breeders work within germplasm that is of a "cultivated variety" or "elite." This germplasm is easier to breed because it generally performs well when evaluated for horticultural performance. Numerous *Brassica oleracea* crop cultivated varieties (cultivars) have been developed, including, but not limited to, broccoli, cauliflower, sprouting broccoli, Brussels sprouts, white cabbage, red cabbage, savoy cabbage, curly kale cabbage, turnip cabbage and Portuguese cabbage. However, the performance advantage a cultivated or elite germplasm provides can be offset by a lack of allelic diversity. Breeders generally accept this tradeoff because progress is faster when working with cultivated material than when breeding with genetically diverse sources.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background to which a *Brassica oleracea* species can be crossed. In addition, the genomic regions associated with disease resistance disclosed herein can be introgressed from one genotype to another and tracked phenotypically or genetically. Thus, Applicants' development of markers for the selection of the disease resistance facilitates the development of *Brassica oleracea* plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment, particularly for traits like disease resistance. The markers provided by the invention offer an effective alternative and therefore represent a significant advance in the art.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. Plants comprising the recombinant DNA molecules and engineered proteins, or plants produced from the cells, tissues or seeds, have curds or heads that exhibit increased resistance to downy mildew. Suitable methods for transformation of host plant cells for use with the current disclosure include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

V. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita, et al., *Genomics* 8:271-278, 1989), denaturing gradient gel electrophoresis (Myers, EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Brassica oleracea* plant a genotype associated with disease resistance, identify a *Brassica oleracea* plant with a genotype associated with disease resistance, and to select a *Brassica oleracea* plant with a genotype associated with disease resistance. In certain embodiments of methods of the invention, polymorphic nucleic acids can be used to produce a *Brassica oleracea* plant that comprises in its genome an introgressed locus associated with disease resistance. In certain embodiments of the invention, polymorphic nucleic acids can be used to breed progeny *Brassica oleracea* plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in *Brassica oleracea* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz, et al., *Genome Res.* 13:513-523, 2003; Cui, et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Brassica oleracea* plants can be regenerated, plant calli, plant clumps and plant cells that are intact in plants or parts of plants such as pollen, flowers, curds, heads, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any plant or variety that has resulted from breeding and selection for superior agronomic performance. An "elite plant" refers to a plant belonging to an elite variety. Numerous elite varieties are available and known to those of skill in the art of *Brassica oleracea* breeding. An "elite population" is an assortment of elite individuals or lines that can be used to represent the state of the art in terms of agronomically superior genotypes of a given crop species, such as a *Brassica oleracea* line. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility of plant curds or heads to downy mildew.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 2500 seeds of cauliflower (*Brassica oleracea*) strain MYCOCLP, which comprises the two downy mildew resistance QTLs on chromosome 3, as described herein. The deposit was made with the American Type Culture Collection (ATCC), 10801 University Boulevard, Manassas, Va. 20110-2209 USA. The deposit is assigned ATCC Accession No. PTA-124338, and the date of deposit was Jul. 28, 2017. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

Example 1

Identification of Downy Mildew Resistance Alleles and Mapping

The resistant source MYCOCLP has been deposited with the ATCC and assigned Accession No. PTA-124338. MycoCLP was crossed with downy mildew sensitive brilliant white cauliflower line BSCLPN to create a mapping population. The resulting F1 plants were used to develop a doubled haploid population. In total, 198 first generation doubled haploid (DH) lines were developed and used for trial evaluation and genotype mapping together with the parental lines as sensitive and resistant controls.

The downy mildew resistance for this mapping population was determined in field locations. Each trial contained 3 replicates with 10 plants for each DH line in each replicate. In these trials, natural downy mildew isolates were relied on to infect the plants. Trials were sown in a time staggered manner in order to anticipate variable natural infection rates, but also to accommodate different rates of heading between the different lines. In this mapping population a difference in head maturation of about one month was observed between the different lines depending on environmental conditions. In a first experiment, six staggered trials were performed with six sowing dates over a six week period in April and May and six planting dates over a six week period in June. Evaluations for this experiment occurred from August through November. In a second experiment, trials were planted at the same time in two locations, with three trials in each location. For these trials, the materials were planted with three sowing dates over a three week period in April and May and three respective planting dates over a three week period in June. These trials were evaluated from August through November.

To determine the rate of downy mildew infection, mature curds were evaluated one week after a grower would normally harvest the crops, which is between three and four months after planting. The curds were harvested and sliced open several times to determine the level of downy mildew present. Subsequently, each plant was given a score of 1 (no symptoms), 5 (some symptoms), or 9 (multiple infection sites and/or >⅓ of the curd infected). For each line, the results from the two experimental trials were combined and the downy mildew score was summarized into the least square mean.

Each DH line was genotyped and QTL analyses were undertaken with MapQTL5 using interval mapping at a 1 cM mapping step size. Significance thresholds were determined by permutation tests with 1000 permutations each and a threshold of $p=0.05$. The QTL mapping analysis identified two QTLs on chromosome 3 that together explain 48.1% of the phenotypic variation around downy mildew resistance in the cauliflower curds (FIG. 1).

To reduce the size of the first QTL (between markers M13 to M20), recombinants were identified using the flanking markers M13 and M20 in the F2 generation of a cross between the same parents as used for the QTL mapping. These recombinants were made homozygous for the recombinant break points in the F3 generation. The F4 generation recombinant families were planted in trials for downy mildew resistance. The trial was replicated in six staggered sowings and plantings and was planted across two locations. By aligning the least square mean level of resistance for each of these recombinant families to their respective recombination breakpoints between M13 and M20, the inventors identified that the region between markers M19 and M20 provided the resistance conveyed by the mapped QTL.

The sequences for the markers described herein are shown in Table 1.

TABLE 1

| Marker | QTL | Position on Proprietary Map (cM) | Position SNP v2.1 (bp) | Marker Size (bp) | SNP Position in Marker (bp) | SNP Change | Sequence |
|---|---|---|---|---|---|---|---|
| M13 | 1 | 78 | Unknown | 121 | 61 | T/C | SEQ ID NO: 1 |
| M19 | 1 | 82 | 15,890,285 | 121 | 61 | G/A | SEQ ID NO: 2 |
| M20 | 1 | 93 | 10,184,762 | 121 | 61 | T/C | SEQ ID NO: 3 |
| M31 | 2 | 127 | 3,226,172 | 121 | 61 | T/A | SEQ ID NO: 4 |
| M33 | 2 | 128 | 3,178,026 | 121 | 61 | G/A | SEQ ID NO: 5 |
| M34 | 2 | 129 | 2,874,663 | 121 | 61 | T/C | SEQ ID NO: 6 |
| M35 | 2 | 131 | 2,354,342 | 121 | 61 | A/G | SEQ ID NO: 7 |
| M36 | 2 | 133 | 2,168,486 | 121 | 61 | C/T | SEQ ID NO: 8 |
| M37 | 2 | 133 | 2,212,440 | 118 | 58 | A/C | SEQ ID NO: 9 |
| M38 | 2 | 133 | 1,973,175 | 121 | 61 | C/A | SEQ ID NO: 10 |
| M39 | 2 | 134 | 1,391,141 | 121 | 61 | T/G | SEQ ID NO: 11 |
| M40 | 2 | 135 | 1,932,167 | 121 | 61 | A/G | SEQ ID NO: 12 |
| M41 | 2 | 135 | 2,091,771 | 84 | 61 | A/G | SEQ ID NO: 13 |
| M42 | 2 | 137 | 1,220,020 | 94 | 61 | A/G | SEQ ID NO: 14 |
| M43 | 2 | 137 | 1,219,392 | 121 | 61 | A/G | SEQ ID NO: 15 |
| M44 | 2 | 137 | 1,221,810 | 121 | 61 | C/T | SEQ ID NO: 16 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A *Brassica oleracea* plant of a cultivated variety, the plant comprising a first introgressed allele and a second introgressed allele on chromosome 3, wherein said first introgressed allele or said second introgressed allele confers to a curd or head of said plant increased resistance to downy mildew compared to a plant not comprising said first introgressed allele and said second introgressed allele, wherein said first introgressed allele is flanked in the genome of said plant by marker locus M19 (SEQ ID NO:2) and marker locus M20 (SEQ ID NO:3) on chromosome 3 or wherein said second introgressed allele is flanked in the genome of said plant by marker locus M31 (SEQ ID NO:4) and marker locus M44 (SEQ ID NO: 16) on chromosome 3, and wherein a sample of seed comprising said first introgressed allele and said second introgressed allele was deposited under ATCC Accession Number PTA-124338.

2. The *Brassica oleracea* plant of claim 1, wherein said *Brassica oleracea* plant is a broccoli, cauliflower, sprouting broccoli, Brussels sprouts, white cabbage, red cabbage, savoy cabbage, curly kale cabbage, turnip cabbage or Portuguese cabbage plant.

3. The *Brassica oleracea* plant of claim 1, wherein the plant is homozygous for said first introgressed allele or said second introgressed allele.

4. A seed that produces the *Brassica oleracea* plant of claim 1.

5. A plant part of the *Brassica oleracea* plant of claim 1, wherein the part comprises the first introgressed allele and the second introgressed allele.

6. The plant part of claim 5, wherein said plant part is a cell, a seed, a root, a stem, a leaf, a fruit, a flower, a curd, a head or pollen.

7. A seed of a *Brassica oleracea* of a cultivated variety comprising an introgression fragment comprising a first chromosomal segment on chromosome 3 from *Brassica oleracea* MYCOCLP flanked by marker M19 (SEQ ID NO: 2) and marker M20 (SEQ ID NO:3) and a second chromosomal segment on chromosome 3 from *Brassica oleracea* MYCOCLP flanked by marker M31 (SEQ ID NO: 4) and marker M44 (SEQ ID NO: 16), wherein a sample of seed comprising said first chromosomal segment and said second chromosomal segment was deposited under ATCC Accession Number PTA-124338.

8. The introgression fragment of claim 7, wherein said fragment confers increased resistance to downy mildew.

9. A method for producing a cultivated variety of a *Brassica oleracea* plant with a curd or head having improved resistance to downy mildew, comprising introgressing into said plant variety a first chromosomal segment and a second chromosomal segment from *Brassica oleracea* MYCOCLP on chromosome 3 that confers improved resistance to downy mildew relative to a plant lacking said introgression, wherein the first chromosomal segment is flanked by marker M19 (SEQ ID NO: 2) and marker M20 (SEQ ID NO:3) and the second chromosomal segment is flanked by marker M31 (SEQ ID NO: 4) and marker M44 (SEQ ID NO: 16), and wherein a sample of seed of said *Brassica oleracea* MYCOCLP was deposited under ATCC Accession Number PTA-124338.

10. The method of claim 9, wherein said introgressing comprises:
    a) crossing a plant comprising said first or second chromosomal segment with itself or with a second *Brassica oleracea* plant of a different genotype to produce one or more progeny plants; and
    b) selecting a progeny plant comprising said chromosomal segment.

11. The method of claim 10, wherein selecting a progeny plant comprises detecting at least a first allele flanked by marker M19 (SEQ ID NO:2) and marker M20 (SEQ ID NO:3) or a second allele flanked by marker M31 (SEQ ID NO:4) and marker M44 (SEQ ID NO:16).

12. The method of claim 9, wherein said plant variety is a broccoli, cauliflower, sprouting broccoli, Brussels sprouts, white cabbage, red cabbage, savoy cabbage, curly kale cabbage, turnip cabbage or Portuguese cabbage plant variety.

13. The method of claim 10, wherein the progeny plant is an F2-F6 progeny plant.

14. The method of claim 10, wherein said crossing comprises backcrossing, wherein said crossing comprises from 2-7 generations of backcrosses or wherein said crossing comprises marker-assisted selection.

15. A *Brassica oleracea* plant produced by the method of claim 9, wherein said plant comprises said first and second chromosomal segment.

16. A method of producing food or feed comprising obtaining a plant according to claim 1, or a part thereof, and producing said food or feed from said plant or part thereof.

17. A method of selecting a *Brassica oleracea* plant exhibiting resistance downy mildew, comprising:
    a) crossing the *Brassica oleracea* plant of claim 1 with itself or with a second *Brassica oleracea* plant of a different genotype to produce one or more progeny plants; and
    b) selecting a progeny plant comprising said first or second introgressed allele.

18. The method of claim 17, wherein selecting said progeny plant comprises identifying a genetic marker genetically linked to said first or second introgressed allele or wherein selecting said progeny plant comprises:
    a) identifying a genetic marker within or genetically linked to a genomic region between marker locus M19 (SEQ ID NO:2) and marker locus M20 (SEQ ID NO:3) on chromosome 3; or
    b) identifying a genetic marker within or genetically linked to a genomic region between marker locus M31 (SEQ ID NO:4) and marker locus M44 (SEQ ID NO:16) on chromosome 3.

19. The method of claim 18, wherein selecting a progeny plant further comprises detecting at least one polymorphism at a locus selected from the group consisting of marker locus M33 (SEQ ID NO:5), marker locus M34 (SEQ ID NO:6), marker locus M35 (SEQ ID NO:7), marker locus M36 (SEQ ID NO:8), marker locus M37 (SEQ ID NO:9), marker locus M38 (SEQ ID NO:10), marker locus M39 (SEQ ID NO:11), marker locus M40 (SEQ ID NO:12), marker locus M41 (SEQ ID NO:13), marker locus M42 (SEQ ID NO:14), and marker locus M43 (SEQ ID NO:15).

20. The method of claim 17, wherein said progeny plant is an F2-F6 progeny plant.

21. The method of claim 17, wherein producing said progeny plant comprises backcrossing.

22. A *Brassica oleracea* plant obtainable by the method of claim 17, wherein said plant comprises said first and second allele.

* * * * *